US008551526B2

(12) United States Patent
Johnston et al.

(10) Patent No.: US 8,551,526 B2
(45) Date of Patent: *Oct. 8, 2013

(54) PREPARATION OF DRUG PARTICLES USING EVAPORATION PRECIPITATION INTO AQUEOUS SOLUTIONS

(75) Inventors: Keith P. Johnston, Austin, TX (US); Robert O. Williams, III, Austin, TX (US); Xiaoxia Chen, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/266,998

(22) Filed: Oct. 8, 2002

(65) Prior Publication Data

US 2004/0067251 A1    Apr. 8, 2004

Related U.S. Application Data

(63) Continuation-in-part of application No. 09/808,332, filed on Mar. 14, 2001, now Pat. No. 6,756,062.

(60) Provisional application No. 60/245,479, filed on Nov. 3, 2000.

(51) Int. Cl.
*A61K 9/16* (2006.01)
*A61K 9/50* (2006.01)
*A61K 9/26* (2006.01)
*A61K 8/00* (2006.01)

(52) U.S. Cl.
USPC ........... 424/489; 424/494; 424/496; 424/497; 424/70.19

(58) Field of Classification Search
USPC ....................................................... 424/489
See application file for complete search history.

(56) References Cited

U.S. PATENT DOCUMENTS

| 5,145,684 | A | * | 9/1992 | Liversidge et al. | 424/489 |
|---|---|---|---|---|---|
| 5,686,133 | A | * | 11/1997 | Amidon et al. | 427/2.22 |
| 5,766,635 | A | | 6/1998 | Spenleuhauer et al. | |
| 5,773,025 | A | * | 6/1998 | Baichwal | 424/458 |
| 5,795,594 | A | | 8/1998 | York et al. | 424/489 |
| 5,851,453 | A | | 12/1998 | Hanna et al. | 264/5 |
| 5,985,248 | A | | 11/1999 | Gordon et al. | 424/46 |
| 6,001,336 | A | * | 12/1999 | Gordon | 424/46 |
| 6,077,543 | A | | 6/2000 | Gordon et al. | 424/489 |
| 6,096,337 | A | * | 8/2000 | Spireas et al. | 424/451 |
| 6,756,062 | B2 | | 6/2004 | Johnston et al. | |
| 6,908,626 | B2 | * | 6/2005 | Cooper et al. | 424/489 |

FOREIGN PATENT DOCUMENTS

| WO | 9714407 | 4/1997 |
|---|---|---|
| WO | 98/29096 | 7/1998 |
| WO | 0247659 A2 | 6/2002 |

OTHER PUBLICATIONS

Liversidge et al., "Particle size Reduction for Improvement of Oral Bioavailability of Hydrophobic Drugs: I. Absolute Oral Bioavailability of Nanocrystalline Danazol in Beagle Dogs", International Journal of Pharmaceutics 125 (1995) 91-97.*
True et al. A novel particle engineering technology to enhance dissolution of poorly water soluble drugs: spray-freezing into liquid, European Journal of Pharmaceutics and Biopharmaceutics 54 (2002) 271-280.*
Sherif et al., Characterization and bioavailability of danazol-hydroxypropyl B-cyclodextrin copreciptates, International Journal of Pharmaceutics 128 (1996) 45-54.*
Reverchon, E. et al., "Supercritical Antisolvent Precipitation of Micro- and Nano-Particles," *Journal of Supercritical Fluids*, vol. 15, 1999, pp. 1-21.
Young, T. J. et al., "Rapid Expansion from Supercritical to Aqueous Solution to Produce Submicron Suspensions of Water-Insoluble Drugs," *Biotechnol. Prog.*, vol. 16, 2000, pp. 402-407.
PCT Publication of International Search Report for PCT/US2001/051337 Dated Jun. 20, 2002, 3 pp.

* cited by examiner

*Primary Examiner* — Michael G Hartley
*Assistant Examiner* — Nabila Ebrahim
(74) *Attorney, Agent, or Firm* — Chainey P. Singleton; Edwin S. Flores; Chalker Flores, LLP

(57) ABSTRACT

A method for preparing poorly water soluble drug particles is disclosed. The method comprises dissolving a drug in at least one organic solvent to form a drug/organic mixture, spraying the drug/organic mixture into an aqueous solution and concurrently evaporating the organic solvent in the presence of the aqueous solution to form an aqueous dispersion of the drug particles. The resulting drug particles are in the nanometer to micrometer size range and show enhanced dissolution rates and reduced crystallinity when compared to the unprocessed drug. The present invention additionally contemplates products and processes for new drug formulations of insoluble drug particles having high dissolution rates and extremely high drug-to-excipient ratios.

5 Claims, 11 Drawing Sheets

T—thermocouple;
P—pressure regulator;
H—HPLC pump

Particle redispersibility in the stability study period

The x-ray peak height of danazol samples during stability study

Surface area of danazol systems during stability study

Dissolution profile of system danazol +PVP 40T+SDS during stability study

Dissolution profile of system danazol +PVP K-15 during

Dissolution profile of system danazol +PVP 40T during stability study

Figure 8: SEM pictures of danazol samples

PVP K-15 +Danazol

PVP 40T +Danazol

PVP 40T +SDS +Danazol

PREPARATION OF DRUG PARTICLES USING EVAPORATION PRECIPITATION INTO AQUEOUS SOLUTIONS

This application is a continuation-in-part of U.S. application Ser. No. 09/808,332 filed Mar. 1, 2001 (U.S. Pat. No. 6,356,062 granted on Jun. 29, 2004) which claims priority to U.S. application Ser. No. 60/245,479 filed on Nov. 3, 2000, under Title 35 of the United States Code section 120.

FIELD OF THE INVENTION

The present invention relates to drug particles and methods for their preparation. More particularly, the present invention relates to the preparation of drug particles utilizing evaporative precipitation into aqueous solutions.

DESCRIPTION OF RELATED ART

Bioavailability is a term meaning the degree to which a drug becomes available to the target tissue after being administered to the body. Poor bioavailability is a significant problem encountered in the development of pharmaceutical compositions, particularly those containing an active ingredient that is poorly soluble in water. Poorly water soluble drugs tend to be eliminated from the gastrointestinal tract before being absorbed into the circulation.

It is known that the rate of dissolution of a particulate drug can increase with increasing surface area, that is, decreasing particle size. Efforts have been made to control the size and size range of drug particles in pharmaceutical compositions For example, wet milling techniques have been used, as described in U.S. Pat. No. 5,145,684. However, such wet milling techniques exhibit problems associated with contamination from the grinding media. It is difficult to produce highly uniform submicron particles with wet milling and solids milling, and handling can be time consuming. Large amounts of surfactants are needed for stabilization resulting in small drug-to-excipient ratios. Moreover, exposing a drug substance to mechanical shear or high temperatures for prolonged periods can cause the drug to lose its activity.

Spray drying into vapor is another method used to form micron sized drug particles. Spray drying is used commonly to formulate dry pharmaceutical powder, In most cases, either hydrophilic drugs in aqueous solution or poorly water soluble drugs in organic solution are sprayed, which approaches do not offer a means to simultaneously spray a poorly water soluble drug and water soluble excipient.

U.S. Pat. No. 5,985,248 teaches dissolving a hydrophilic excipient, or stabilizer, and a hydrophobic drug in a cosolvent system such as water:ethanol, and spray drying the system into vapor. U.S. Pat. No. 6,001,336 teaches suspending a hydrophobic drug in an aqueous solution containing a hydrophilic stabilizer, and spray drying the suspension into vapor. U.S. Pat. No. 6,077,543 and WO 98/29096 teach atomizing an organic and an aqueous solution together into a vapor. In all of these teachings, drug particles in the micron size range are formed. It is difficult to produce sub-micron particles by these technique due to growth of the drug particles during the solvent evaporation. As the water evaporates it will no longer solvate hydrophilic stabilizers. Solvation of the stabilizer is needed for it to be able to prevent growth of the drug particles. As a result, growth of the drug particles is not likely to be inhibited by the stabilizer and the particle size is typically greater than 1 micron. Moreover, in all of these teachings, the precipitation of surfactant, or other excipient, and stabilizers occur simultaneously in the coaxial nozzle, and it is much more difficult to control the particle morphology. Furthermore, in all of these teachings, the useful excipients are sugars, salts, pectin and citric acid, which are not good stabilizers for preventing growth of particles during the spray process.

U.S. Pat. Nos. 5,795,594 and 5,851,453 teach the use of compressed fluid antisolvents to form drug particles in the micron-size range. This process has been called Precipitation using Compressed Antisolvents (PCA), Solution-Enhanced Dispersion of Solids (SEDS) and Supercritical AntiSolvent process (SAS). In most cases this process does not utilize water due to the low solubility of water in compressed carbon dioxide, so that it is difficult to use water-soluble excipients with this process. However, in some cases, this process is able to use water by flowing an organic drug solution, an aqueous solution and a second organic solvent such as ethanol into compressed carbon dioxide. The ethanol is needed to extract the water into the CO2 phase. In this process it is difficult to control the particle size due to the complexity of the mixing of the three streams in the jet. Also, the particles must be recovered from a high pressure vessel, and high ratios of CO2 to drug are necessary. Moreover, as the water contacts CO2, the pH in the water reaches 3, which can be detrimental to drug stability and interactions with excipients.

Young et al., *Rapid Expansion from Supercritical to Aqueous Solution to Produce Submicron Suspensions of Water-Insoluble Drugs*, Biotechnol. Prog. 2000, 16, 402-407, teach the formation of poorly water soluble drug particles by rapid expansion of supercritical fluid solutions into water, the supercritical fluid was carbon dioxide above its critical temperature. The solubility of drugs in carbon dioxide and other supercritical fluids such as ethane and propane is typically very small. It is difficult to add water soluble stabilizers and excipients in spray antisolvent processes (PCA, SAS or SEDS) into carbon dioxide due to the low solubility of water in CO2. Reverchon E., *Supercritical Antisolvent Precipitation of Micro-and Nano-particles*, J. Supercrit. Fluid., 1999, 15, 1-21. These antisolvent processes require large ratios of carbon dioxide to drug and the use of a high pressure vessel for recovery of product. Even when an aqueous and two organic solutions are sprayed through a coaxial nozzle, the process is subject to many of the limitations discussed above for spray drying organic and aqueous phases through coaxial nozzles. As the water dissolves into the ethanol-carbon dioxide mixture, it is no longer available to solvate stabilizers to prevent particle growth. Therefore this process is limited to relatively few drugs.

It would be an advantage in the art of preparation of drug particles to provide a method which allows for easy control of particle size and morphology and which is applicable to a wide breadth of drug substances.

An additional challenge for poorly water soluble drugs is to achieve high dissolution rates with a high drug-to-excipient ratio or high payload. From a therapeutic point of view, drug formulations with high drug-to-excipient ratios, or payloads, have many advantages. First, such formulations allow an effective dose to be used to produce high levels of local drug concentration with greater therapeutic efficiency. Second, high drug loading results in less coadministration of the excipients, thereby minimizing potential biological reaction to such excipients. Excipients are used to increase the dissolution rates of poorly water soluble drugs. Known techniques use a drug to excipient ratio on the order of 1:1, for example, the Nanocrystal technology of Elan pharmaceuticals.

Therefore, there remains a need for drug formulations and techniques that allow for enhanced drug potency leading to greater therapeutic efficiency for poorly water soluble drugs. Accordingly, achieving immediate release with a high drug-to-excipient ratio is desirable.

SUMMARY OF THE INVENTION

In one aspect, the present invention is a method for preparing poorly water soluble drug particles comprising the steps of dissolving a drug in at least one organic solvent to form a drug/organic mixture; spraying the drug/organic mixture into an aqueous solution; and concurrently evaporating the organic solvent in the presence of the aqueous solution to form an aqueous dispersion of the drug particles.

In a second aspect, the present invention is poorly water soluble drug particles having an average particle diameter of from 50 nanometers to 20 microns, the drug particles being prepared by a process comprising the steps of dissolving the drug in at least one organic solvent to form a drug/organic mixture; spraying the drug/organic mixture into an aqueous solution; and concurrently or rapidly evaporating the organic solvent in the presence of the aqueous solution to form an aqueous dispersion of the drug particles.

In another aspect, the present invention provides for drying or otherwise removing water or other excipients from the aqueous dispersion of drug particles. The drying may be accomplished by any known method of removing water or other excipient(s) from particles including, but not limited to, lyophilization, vacuum drying, spray drying, or the like. In another aspect of the invention, water removed is facilitated prior to drying, such as for example and without limitation, by centrifugation, filtration, settling, anti-solvent or flocculating agent, a gelation agent, an adsorbent, a solid matrix or solid particles that the particles adhere to, or the like.

Another aspect of the present invention provides poorly water soluble drug particles with high drug:excipient ratios; high dissolution rates; high potency; or high surface areas. In an exemplary case herein, formulation of such micron or sub-micron size drug particles were produced by evaporative precipitation into an aqueous solution containing the excipient.

In certain aspects, the present invention utilizes evaporative precipitation into aqueous solutions (EPAS) to form micron to sub-micron sized drug particles, leading to increased bioavailability relative to larger particles. The process of the present invention has applicability to a wide range of drug substances as several solvents may be chosen to dissolve the drug. The ability to utilize poorly soluble drugs and water soluble stabilizers/excipients offers the ability to form submicron particles that have high dissolution rates in aqueous media. The present invention also offers the ability to better control the resulting particle size and morphology relative to techniques described in the above identified prior art. Moreover, the present invention often produces particles having reduced crystallinity as compared to the bulk, unprocessed drug, which enhances dissolution.

BRIEF DESCRIPTION OF THE FIGURES

FIG. 13($b$) is a graphic illustration of the dissolution profile of system danazol+PVP K-15 during stability study.

FIG. 13($c$) is a graphic illustration of the dissolution profile of system danazol+PVP 40T during stability study.

DETAILED DESCRIPTION OF THE INVENTION

Figure 1:
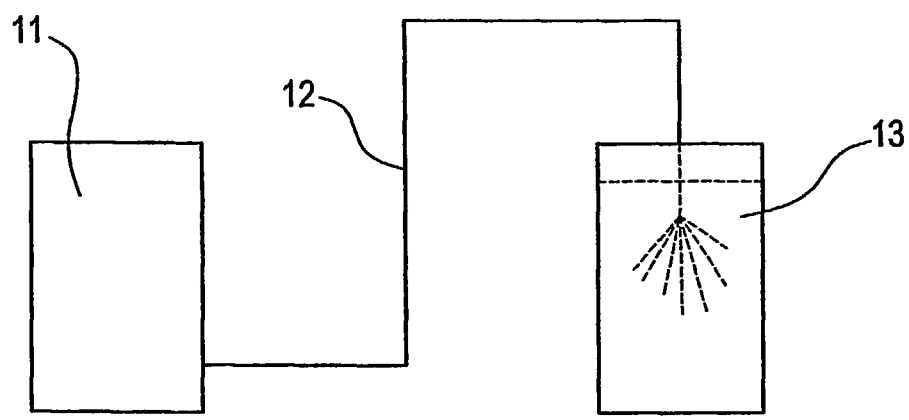
FIG. 1 is a schematic diagram illustrating one embodiment of the process of the present invention.

FIG. 1 is a schematic diagram illustrating one embodiment of an apparatus useful for the process of the present invention. As shown, tank 11 contains a drug/organic mixture.

The drug/organic mixture is formed by dissolving a drug in at least one organic solvent. The resulting drug/organic mixture can be a solution, an emulsion or a microemulsion.

The drug which can be used in the process of the present invention can be any poorly water soluble drug. Suitable drug substances can be selected from a variety of known classes of drugs including, for example, analgesics, anti-inflammatory agents, anthelmintics, antianginal agents, anti-arrhythmic agents, antibiotics (including penicillins), anticoagulants, antidepressants, antidiabetic agents, antiepileptics, antigonadotropins, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiacinotropic agents, contrast media, cortieosterioids, cough suppressants (expectorants and mucolytics), diagnostic agents, diagnostic imaging agents, diuretics, dopaminergics (antiparkinsonian agents), haemostatics, immunosuppressive cyclic oligopeptides, immunological agents, lipid regulating agents, muscle relaxants, parasympathomimetics, parathyroid calcitonin and biphosphonates, radio-pharmaceuticals, sex hormones (including steroids), anti-allergic agents, stimulants and anorexics, sympathomimetics, thyroid agents, vasidilators and xanthines. Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989. More specific examples of drug substances useful in the practice of the present invention include but are not limited to danazol, cyclosponine, nifedipine, carbamazepine, naproxen, triamcinolone and its salts, hydrocortisone and its salts, prednisone and its salts, phenylbutazone, betamethasone and its salts, dexamethasone and its salts, 17-β estradiol, ketoprofen, verapamil, ketoconazole, mefenamic acid, and metronidazole.

The organic solvent into which the drug is dissolved can be any organic solvent which dissolves the drug to an adequate level. Preferably, the organic solvent dissolves the drug to a level of 0.1 weight percent or more, and more preferably to a level of 1.0 weight percent or more. The organic solvent is advantageously immiscible with water. Suitable organic solvents include diethylether, methylene chloride, ethyl acetate, dimethylether, perfluoroalkanes and isomers thereof, partially fluorinated solvents with or without other functional groups, and other organic solvents with boiling points below approximately 70° C., and combinations thereof.

In one embodiment, the drug/organic mixture further contains a particle stabilizer. Stabilization is defined herein to mean that the resulting drug particles do not grow substantially, and do not crystallize excessively. In this regard, a particle stabilizer is defined herein to mean a substance that substantially inhibits particle growth and substantially inhibits crystallization of the drug particles. The particle stabilizer can be water soluble or organic soluble, although, if the particle stabilizer is water soluble, bioavailability may be enhanced to an even greater degree. Particle stabilizers can also act as absorption enhancers in order to increase bioavailability of the drug particles.

The particle stabilizer present in the organic can contribute to stabilization of the particle in the aqueous phase. Examples of particle stabilizers include phospholipids, surfactants, either low molecular weight or polymeric, vesicles, polymers, including copolymers and homopolymers and biopolymers, and/or dispersion aids. The particle stabilizer can be nonionic, anionic, cationic or zwitterionic. Suitable surfactants include gelatin, casein, lecithin, (phosphatides), gum acacia, cholesterol, tragacanth, stearic acid, benzalkonium chloride, calcium stearate, glyceryl inonostearate, cetostearyl alcohol, cetomacrogol 1000, polyoxyethylene castor oil derivatives, polyoxyethylene sorbitan fatty acid esters, for example, the commercially available Tweens, polyethylene glycols, copolymers of polyethylene glycol and polypropylene glycol, polyoxyethylene stearates, colloidal silicon dioxide, phosphates, sodium dodecylsulfate, carboxymethicellulose calcium, carboxymethylecellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinylalcohol, sodium lauryl sulfate.(SLS), polyvinylpyrrolidone (PVP), bile salts.

Referring again to FIG. 1, the drug/organic mixture is fed through feed line 12 to a sprayer, where the drug/organic mixture is sprayed into an aqueous solution contained in tank 13. The drug/organic mixture is sprayed at or below the liquid level of the aqueous solution in tank 13.

In one alternative embodiment of the present invention, a portion of the aqueous solution can be sprayed together with the drug/organic mixture into the remaining portion of the aqueous solution. In such an embodiment, the nozzle should be designed so as to allow the spraying of two streams simultaneously. In such an embodiment, the level of the aqueous solution in tank 13 can be controlled by, for example, an overflow, such that a continuous slurry of particles results. The slurry of particles can then undergo further processing to result in the final drug particles.

Figure 2:
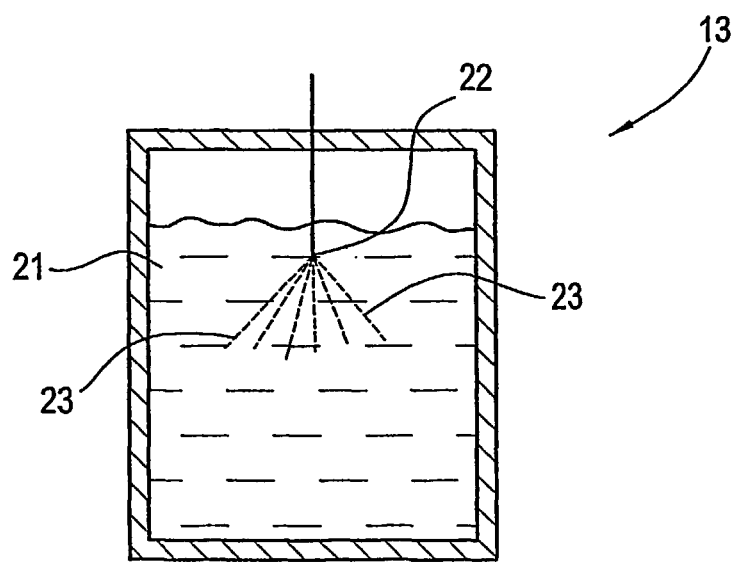
FIG. 2 is a cross-sectional view of a vessel useful in the process of the present invention.

FIG. 2 is a cross-sectional view of tank 13 containing aqueous solution 21. In a preferred embodiment, aqueous solution 21 contains at least one particle stabilizer. Suitable particle stabilizers include those listed above for inclusion in the drug/organic mixture, The specific particle stabilizer or particle stabilizers selected for use in the aqueous solution 21 can be the same or can be different from the particle stabilizer(s) in the drug/organic mixture. The weight ratio of drug to total particle stabilizer is from 0.01:1 to 10:1, preferably from 0.05:1 to 7:1 and more preferably from 0.1:1 to 4:1.

The drug/organic mixture is sprayed at or below the liquid level in tank 13 through atomizer 22 to form a jet comprising droplets 23. The jet results in intense mixing between the drug/organic mixture droplets and the aqueous solution. Thus, as the drug/organic mixture is sprayed through atomizer 22, the organic solvent is concurrently evaporated into the aqueous solution 21 to form an aqueous dispersion of the drug particles. In this manner, evaporation of the organic solvent is occurring rapidly with the spraying and stabilization of the drug particles by the excipients in the aqueous solution. Evaporation of the organic solvent occurs below the surface of the aqueous solution. An excipient is any substance combined with an active ingredient to prepare a dosage composition. One example of an excipient is a surfactant which is a compound that reduces the surface tension of liquids, or reduces the interfacial tension between two liquids or a liquid and a solid. Excipients of the present invention may be used individually or in combination. In addition, excipients may be electrostatic or stearic or any combination of electrostatic and stearic.

Atomizer 22 can be any device that is capable of breaking up a bulk liquid into droplets. Suitable devices useful as atomizers include pressure nozzles, venturi nozzles, vibrating orifices, ultrasonic spray nozzles, rotating cups or disks, bubble caps or grids, or perforated plates.

The atomization of the evaporating organic solution into small droplets in the water and the intensity of the spray produce intense mixing between the growing drug particles and the water-soluble stabilizers and excipients. The rapid evaporation of the organic solvent produces large supersaturation of the drug and rapid precipitation. The rapid precipitation of the drug has the potential to produce amorphous instead of crystalline particles as the time frame is too short for crystallization. The hydrophilic stabilizers remain solvated by water during the evaporation of the organic solvent. Thus, the stabilizers cover the growing drug particles and varying the flow rate, nozzle geometry, concentration of drug and stabilizer and the nature of the stabilizer(s).

The temperature of the drug/organic mixture is at a level which allows for rapid evaporation of the solvent. Typically, this temperature will be at least 50 degrees centigrade (° C.) below the normal boiling point of the organic solvent to 80° C. above the normal boiling point of the organic solvent. If the temperature of the drug/organic mixture is at or above its normal boiling point, feed line 12 must be at sufficient pressure to maintain a liquid phase.

The temperature of the aqueous phase is preferably at least 10° C., more preferably at least 50° C., and even more preferably at least 70° C. The upper temperature limit will depend upon the operating pressure, but is preferably low enough so as not to degrade the drug, but high enough to evaporate the solvent but not evaporate too much of the water. In a preferred embodiment, the temperature is less than 120° C., more preferably less than 95° C., and even more preferably less than 85° C. The pressure of the aqueous solution can be at ambient pressure, below ambient pressure to facilitate evaporation or above ambient pressure.

In the present invention, the drug particles are produced in a liquid aqueous phase rather than a gas phase. Therefore, the particle growth is inhibited by aqueous stabilizers that do not precipitate. The dissolution rates of the drug particles coated with water soluble stabilizers may be expected to be high since the dispersions come from an aqueous phase. In the present invention the particle formation stage is distinct from stage in which the aqueous solution is dried. Therefore the present invention can provide greater control over particle size.

The average particle diameter of the particles in the aqueous dispersion are from 50 nanometers to 20 microns, more preferably from 100 nanometers to 5 microns, and even more preferably from 200 nanometers to 1 micron. The drug particles are not necessarily spherical. Average particle diameter can be measured using any technique known to those skilled in the art, such as sedimentation field flow fractionation, photon correlation spectroscopy, disk centrifugation or dynamic light scattering techniques.

An advantage of the present invention is the narrow polydispersity, also referred to as particle size distribution, that results. The particle size distribution is typically monomodal, with narrow size ranges.

As an additional advantage, it is believed that drug particles prepared according to the present invention can exhibit reduced crystallinity as compared to the bulk, unprocessed drug. Such reduced crystallinity can lead to increased dissolution rates and bioavailability.

The process of the present invention desirably further comprises the step of recovering the drug particles. In one embodiment, recovering the drug particles comprises removing the water from the particles. Removing the water can be performed using any technique known to those skilled in the art, including spray drying, spray freeze drying, gellation, defined as gelling the particles within a polymeric matrix, lyophilization, drying with cold air, and filtration.

Advantageously, excipients can be added to either the drug/organic mixture or to the aqueous solution, either before or after the drug particles are formed, in order to enable the drug particles to be homogeneously admixed for appropriate administration. Suitable excipients include polymers, absorption enhancers, solubility enhancing agents, dissolution rate enhancing agents, stability enhancing agents, bioadhesive agents, controlled release agents, flow aids and processing aids. More particularly, suitable excipients include cellulose ethers, acrylic acid polymers, and bile salts. Other suitable excipients are described in detail in the Handbook of Pharmaceutical Excipients, published jointly by the American Pharmaceutical Association and The Pharmaceutical Society of Great Britain, the Pharmaceutical Press, 1986. Such excipients are commercially available and/or can be prepared by techniques known in the art.

Figure 13:
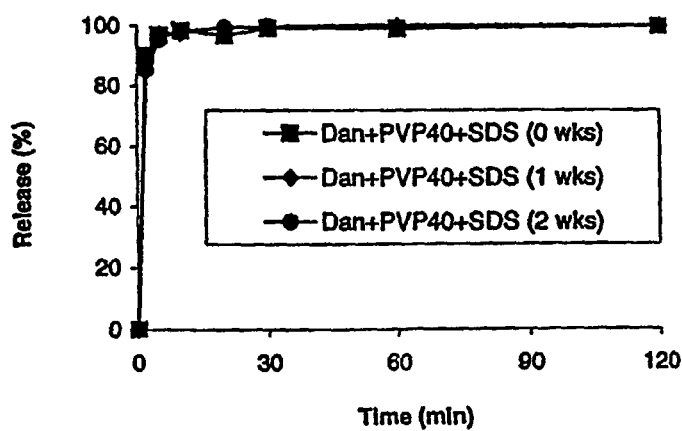
FIG. 13($a$) is a graphic illustration of the dissolution profile of system danazol+PVP 40T+SDS during stability study.
Figure 13:
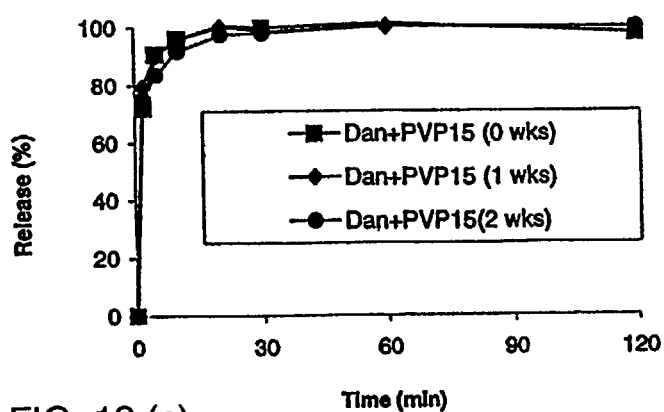
Figure 13:
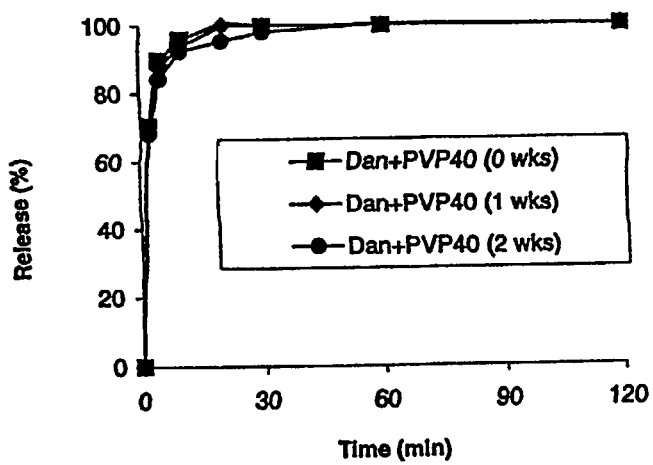

An additional embodiment of the present invention involves poorly water soluble drug particles having high dissolution rates; high drug-to-excipient ratios; high potency; or high surface area. The dissolution rate, according to this invention, is the time necessary to achieve a percentage of particle dissolution at a rate faster than that achieved by the bulk drug under similar conditions, where the bulk drug is approximately 99% pure without excipients. Dissolution rates, according to this invention, are greater than about 70%; perhaps greater than 80%; preferably greater than 90%; more preferably greater than 95%; and most preferably 100% of the drug particles dissolved within a period of time 3 times faster than that of the bulk drug. Alternatively such dissolution rates may be obtained within a period of time about 5 or 7 times faster; preferably within a period of about 10 or 15 times faster; more preferably within a period of about 20 or 25 times faster; most preferably within a period of 30 times faster; and perhaps even faster when compared to that of the bulk drug. Exemplary dissolution profiles are depicted at FIGS. 13(*a*)-(*c*).

The poorly water soluble drug particles of the present invention can possess a drug-to-excipient ratio of about 2:1, although it is preferable for the drug-to-excipient ratio to be 3:1 or greater, more preferably about 4:1, 5:1, 6:1, 7:1, 8:1, 9:1 or greater, and most preferably about 10:1 or perhaps even greater.

In an alternative aspect, the present invention provides poorly water soluble drug particles that are highly potent, where potency is expressed as a percentage (wt. drug/(wt. drug+wt. excipient)). The potent particles of this invention have a potency of greater than about 50%, and perhaps about 66% or greater, preferably greater than about 70% or 75%, more preferably greater than about 80%, 83%, 85% or 87%, most preferably greater than about 90%, 91%, 92%, 93%, 94%, 95%, 96%, 97%, 98%, 99%, or 100%.

Another aspect of the present invention provides poorly water soluble drug particles that possess high surface area. The surface areas exhibited by particles of this invention are greater than about 2.5 $m^2/g$, perhaps even greater than about 5 $m^2/g$, preferably greater than about 10 $m^2/g$, more preferably greater than about 20 $m^2/g$, and most preferably greater than about 30 $m^2/g$.

The poorly water soluble drug particles of the present invention can be amorphous, crystalline or semi-crystalline. Amorphous meaning primarily amorphous in structure, crystalline meaning primarily crystalline in structure and semi-crystalline meaning any mixture of amorphous and crystalline domains.

The disclosed poorly water soluble drug particles can be produced by any method including solution precipitation, spray processes, wet milling, mechanical milling, anti-solvent based precipitation, or other methods in which atomization of drug particles and excipient adsorption are employed. While any technique may be utilized, spray freezing or evaporative precipitation into an aqueous solution is the preferred method.

In another aspect the present invention provides a broad range of liquid dosage form pharmaceutical composition made from the disclosed poorly water soluble drug particles including those produced by the methods disclosed herein. Specifically, the present invention includes any of the disclosed poorly water soluble drug particle dispersions, combined with any pharmaceutically appropriate excipients, for delivery to a subject. Appropriate pharmaceutical excipients include particle stabilizers, tonicity adjusters, buffers, surfactants, mucoadhesive agents, viscosity adjusting agents and other excipients that are known in the art to prepare dispersions for pharmaceutical administration. Specific liquid or similar dosage forms that are contemplated include nebulization, parenteral, topical creams, emulsions, lotions and the like, or transdermal administration forms. Specifically parenteral administration routes contemplated include dispersions administered intraveneously, intramuscularly, subcutaneously, intradermally, intrathecally, and may additionally comprise buffers, tonicity agents, biodegradable polymers, preservatives and other excipients that are known in the art to prepare dispersions suitable for parenteral administration. Moreover, it is contemplated that the dispersions may be administered as an oral liquid, and comprise flavoring agents, sweetening agents, bulking agents, buffers, preservatives, tonicity adjusting agents, particle stabilizers, agents to modify the zeta potential and other excipients that are known in the art to prepare dispersions for oral administration. As a liquid, no reconstitution is required. In addition, dispersions according to the invention may be formulated for administration topically to the eye to treat surface or intraocular conditions, and may comprise buffers, preservatives, tonicity adjusting agents, particle stabilizers, viscosity modifiers and other excipients that are known in the art to prepare dispersions for application to the eye. Also, the dispersions contemplated herein may be formulated for administration topically to the skin, surface of the eye, ear, nasally, vaginally or rectally as an ointment, cream or gel, and may comprise buffers, preservatives, tonicity adjusting agents, particle stabilizers, viscosity modifiers and other excipients that are known in the art to prepare dispersions for application to the area. It is further contemplated that the dispersion may be formulated for administration in a transdermal patch comprising adding the dispersion with polymers, gelling agents, absorption enhancing agents, particle stabilizers, adhesive agents and other excipients While the invention is described herein primarily in connection with its preferred utility, i.e., with respect to micro and nanoparticulate drug substances for use in pharmaceutical compositions, it is also believed to be useful in other applications such as the formulation of particulate cosmetic compositions and the preparation of particulate dispersions for use in image and magnetic recording elements.

The following examples are for illustrative purposes only and are not intended to limit the scope of the claimed invention. Percentages are in weight percents unless otherwise stated.

EXAMPLES

For the following examples, the apparatus shown in FIG. 1 is used. The drug/organic mixture was fed via a Constametric 3200 HPLC pump through a preheating coil into a 30 mL receiving tank containing the required amount of aqueous solution. The nozzle used for the spraying was made by cutting 1/16" stainless steel tubing to form an elliptical conical geometry at the end. The end of the tube was filed to obtain the desired flow rate. Nitrogen was continuously flowed downward to break up foam in cases where it formed. For all of the examples, particle size was measured by dynamic light scattering techniques within 4 hours of the spray.

Dissolution testing for the following examples was carried out using a Vankel dissolution apparatus following the USP Apparatus II paddle method. During all dissolution tests, to ensure sink conditions, only 10-30 percent of the saturation solubility of the drug was added to the dissolution apparatus. The appropriate amount of final drug preparation was weighed and added to 900 ml of distilled water. Each sample was stirred at 50 rpm using a paddle-type stirrer. The dissolution apparatus was maintained at 37° C. throughout the experiment. Samples in the amount of 5 ml were automatically withdrawn at 10, 20, 30 and 60 minute intervals. These samples were filtered using a 0.45 μm filter (Gelman OHP Acrodisc 0.45 μm, VWR). To ensure that no precipitation occurred during HPLC analysis, 0.5 ml of organic solvent was added to 3 ml of filtered sample. This organic solvent was preferably the organic component in mobile phase (acetonitrile). These were mixed using a vortex mixer at high speed for approximately 10 seconds and then refiltered using a 0.45 μm filters into a HPLC vial for analysis. HPLC analysis was different for each drug and the exact methods being modified from those suggested in 'HPLC methods for pharmaceutical analysis' by George Lunn and Norman R. Schmuff, John Wiley & Sons, NY, 1997.

Examples 1-8

The drug was cyclosporine, the organic was diethylether, and the concentration of the drug/organic mixture was 5.0 weight percent cyclosporine in diethylether. For the aqueous solution, Tween-80, a polyoxyethylene sorbitan monolaurate (ACROS) was a surfactant, or other excipient, which was used as the particle stabilizer. The drug/organic mixture was sprayed into 10 mL of aqueous solution at a rate of 1 ml/min. Table A lists processing parameters and the resulting particle sizes.

TABLE A

| Ex | Drug/organic temp. (° C.) | Aqueous temp (° C.) | Spray time (min) | Tween-80 conc (wt percent) | Median particle size (nm) | percent particles <median size |
|---|---|---|---|---|---|---|
| 1 | 65 | 55 | 10 | 1 | 470 | 11 |
| 2 | 65 | 55 | 10 | 1 | 608 | 64 |
| 3 | 65 | 65 | 10 | 1 | 1114 | 61 |
| 4 | 65 | 65 | 10 | 1 | 759 | 41 |
| 5 | 70 | 65 | 10 | 1 | 706 | 33 |
| 6 | 70 | 65 | 10 | 1 | 796 | 43 |
| 7 | 70 | 65 | 10 | 1 | 932 | 50 |
| 8 | 70 | 65 | 20 | 5 | 322 | 14 |

Examples 9-13

The drug was cyclosporine, the organic was diethylether, and the concentration of the drug/organic mixture was as shown below in Table B. For the aqueous solution, phosphatidyl choline (10 wt percent), a Sigma egg lecithin, 60 percent pure, was a surfactant, or other excipient, used as a particle stabilizer. The drug/organic mixture was sprayed into 10 mL aqueous solution at a rate of 1 ml/min. The temperature of the aqueous solution is 75° C., while the drug/organic mixture was sprayed into the aqueous solution at a temperature of 75° C. Table B lists some processing parameters and the resulting particle sizes.

TABLE B

| Ex | Drug conc in organic soln (wt percent) | Spray time (min) | Drug conc in aqueous (mg/ml water) | Drug/surfactant ratio | Particle size range (nm) |
|---|---|---|---|---|---|
| 9 | 1 | 20 | 14.5 | 0.13 | 135-390 |
| 10 | 2 | 19 | 30.8 | 0.28 | 120-575 |
| 11 | 5 | 10 | 37.1 | 0.33 | 90-300 |
| 12 | 5 | 10 | 34.9 | 0.32 | 215-590 |
| 13 | 10 | 6 | 29.7 | 0.30 | 170 |

Examples 14-16

The drug was cyclosporune (5 wt percent), the organic solvent was that listed in Table C below. For the aqueous solution, Poloxamer 407(1 wt percent), also known as Lutrol-F127, a poly(ethylene)-poly(propylene) block polymer consisting of 73 percent of polyethylene glycol and 27 percent polypropylene glycol with an average molecular weight of 12,000 (BASF), was a surfactant, or other excipient, used as a particle stabilizer. The drug/organic mixture was sprayed into 25 mL aqueous solution at a rate of 1 ml/min. The temperatures of the aqueous solution and of the drug/organic mixture were 75° C. Table C lists some processing parameters and the resulting particle sizes.

TABLE C

| Ex | Organic Solvent | Drug conc in aqueous (mg/ml water) | Drug/surfactant ratio | Particle size range (nm) |
|---|---|---|---|---|
| 4 | Diethyl Ether | 15 | 1.5 | 320-1000 |
| 15 | Dichloromethane | 17.8 | 1.78 | 160-345 |
| 16 | Dichloromethane | 14.8 | 1.48 | 196-202 |

Examples 17-21

The drug was danazol, and the solvent was methylene chloride. The particle stabilizer in the aqueous solution is listed below in Table D. In all cases, the concentration of the particle stabilizer in aqueous solution was 1 weight percent. The drug/organic mixture (2 wt percent drug) was sprayed into the aqueous solution at a rate of 2 ml/minute for 5 minutes. The temperature of both the aqueous solution and the drug/organic mixture was 75° C. The drug/excipient ratio was 1.06.

TABLE D

| Ex | Particle stabilizer | Particle size range (nm) |
|---|---|---|
| 17 | Sodium lauryl sulfate | 370-415 |
| 18 | Poly (vinyl pyrolidone) | 140-280 |
| 19 | Poly (vinyl pyrolidone) | 315-450 |
| 20 | Poloxamer | >1000 |
| 21 | *Myrj 52 | >1000 |

*Myrj is polyoxyethylene monostearate

Examples 22-26

The drug was Carbamazepune, and the solvent was methylene chloride. The concentration of drug in the organic was 2 weight percent. The particle stabilizer in the aqueous solution is listed below in Table E. In all cases, the concentration of the particle stabilizer in aqueous solution was 1 weight percent. The drug/organic mixture was sprayed into the aqueous solution at a rate of 2.5 ml/min. The temperature of both the aqueous solution and the drug/organic mixture was 75° C. The drug/excipient ratio was 1:30.

TABLE E

| Ex | Particle stabilizer | Particle size range (nm) |
|---|---|---|
| 22 | Sodium lauryl sulfate (SLS) | >7000 |
| 23 | Poly (vinyl pyrolidone) (PVP) | 320-1000 |
| 24 | Polyethylene glycol | 290-550 |
| 25 | Poloxamer | >1000 |
| 26 | Myrj 52 | >1000 |

Examples 27-29

Figure 3:
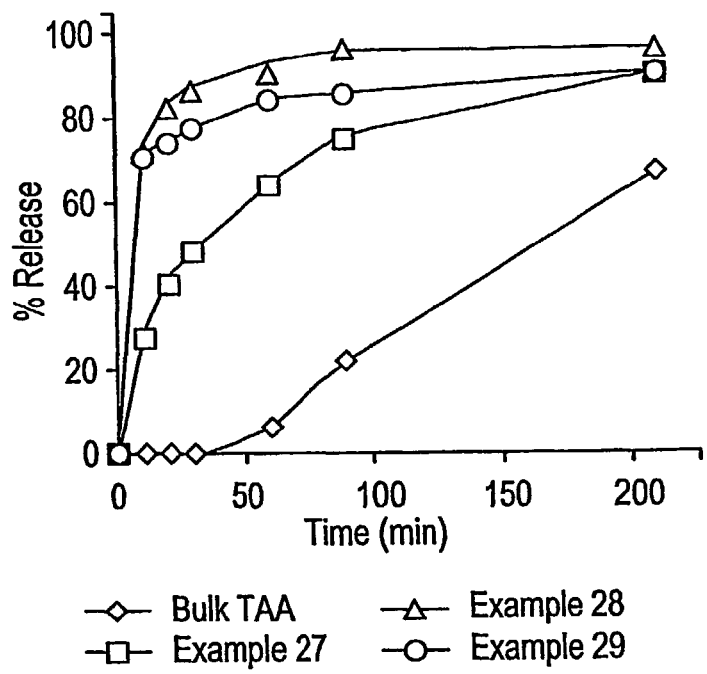
FIGS. 3-4 are graphs showing improved dissolution rates for particles of the present invention.

The drug was Triamcinolone acetonide, also referred to herein as TAA, and the solvent was methylene chloride. The concentration of drug in the organic was 0.5 weight percent. The particle stabilizers in the aqueous solution and the organic solution are listed in Table F. In all cases the concentration of the particle stabilizer in the aqueous solution was 1 Weight percent and in the organic solution was 0.5 weight percent. The volume of the aqueous Solution was 15 ml. In all cases the resulting aqueous drug suspension was poured into a Hydroxypropylmethyl cellulose (HPMC) (grade E-5), thoroughly mixed by hand, poured into a Glass crystallization dish and vacuum dried for at least 10 hours at temperatures ranging from 40-60° C. and a vacuum level of 30 inches of Hg. The resulting solids were mechanically ground to a powder and dissolution studies were performed on these powders. The results of these dissolution tests were compared with that for bulk TAA. The results shown in FIG. 3 indicate the increased dissolution rates of TAA processed according to the present invention.

TABLE F

| Ex | Organic stabilizer | Aqueous stabilizer | Amount of HPMC added for gellation (g) |
|---|---|---|---|
| 7 | PVP K-15 | Deoxycholic acid | 3 |
| 28 | Poloxamer 407 | PVP K-15 | 2 |
| 29 | Poloxamer 407 | Deoxycholic acid | 2 |

Examples 30-32

Figure 4:
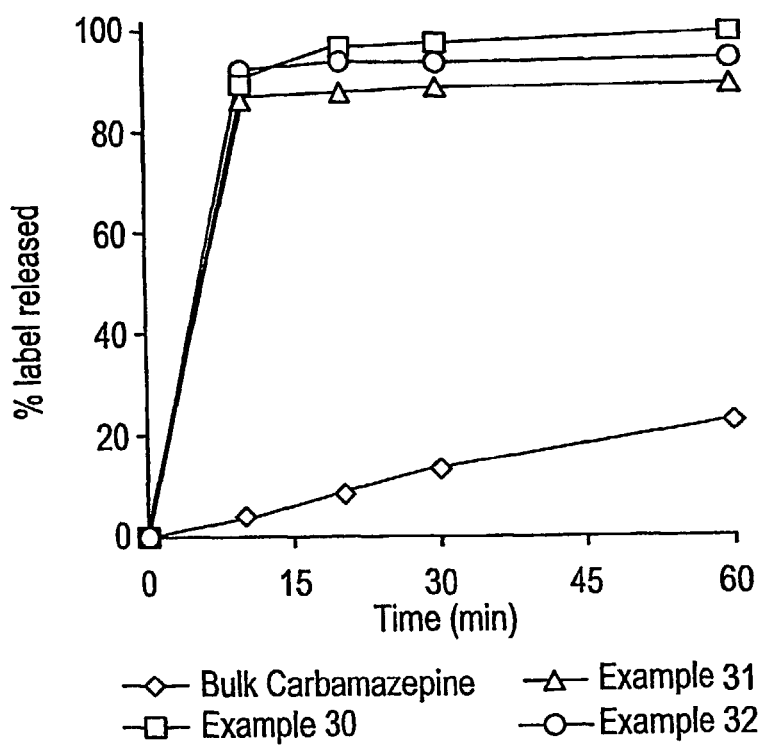

The drug was carbamazepine and the solvent was methylene chloride, The temperature of the drug/organic mixture and the receiving aqueous solution was 87° C. The concentration of drug in the organic was 1.0 weight percent. The particle stabilizers in the aqueous solution are listed in Table G. In all cases the concentration of the particle stabilizer in the aqueous solution was 2 weight percent and the organic solution contains, in addition to the drug, 0.5 weight percent Poloxamer 407. The volume of the aqueous solution was 20 ml. In all cases the resulting aqueous drug suspension was sprayed into liquid nitrogen and the frozen particles were then lyophilized for 24 hours. The resulting powder was thoroughly mixed and dissolution studies were performed on these powders. The results of these dissolution tests were compared with those for bulk carbamazepine. The results shown in FIG. 4 clearly indicate the increased dissolution rates of carbamazepine processed according to the present invention over the bulk unprocessed carbamazepine. The crystallinity of these powders was also studied, with the result being a reduction in crystallinity as compared to the bulk drug.

TABLE G

| Ex | Aqueous stabilizer |
|---|---|
| 30 | Deoxycholic acid |
| 31 | PVPK-15 |
| 32 | SLS |

Example 33

Figure 5:
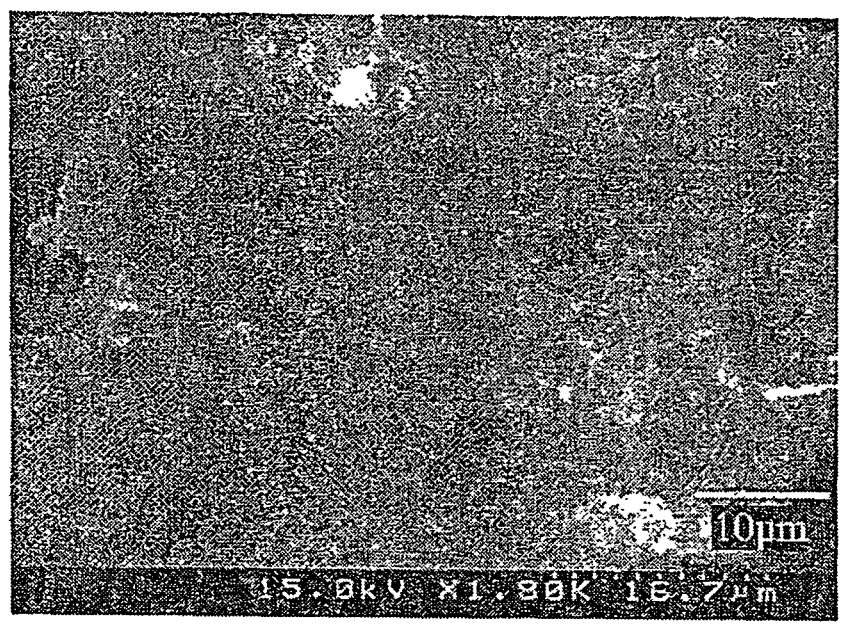
FIG. 5 is an SEM showing reduced crystallinity of the particles of the present invention.

The drug was carbamazepine and the solvent was methylene chloride. The temperature of the drug/organic mixture and the receiving aqueous solution was 87° C. The concentration of drug in the organic was 1.0 weight percent. The particle stabilizer in the aqueous solution was 2 weight percent deoxycholic acid and that in the organic solution was 5 weight percent Poloxamer 407. The organic solution was sprayed at 2 ml/min for 27 minutes into 50 ml of the aqueous deoxycholic acid solution. The suspension was immediately spray dried in a Buchi 190 spray dryer where an inlet temperature of 145-150 degrees C. and an outlet temperature of 90-95° C. were maintained. The resulting dry powder was collected, and an SEM micrograph of this powder is shown in FIG. 5. The Figure shows no crystalline particles indicating the amorphous nature of the drug produced using EPAS.

Examples 34-37

Figure 6:
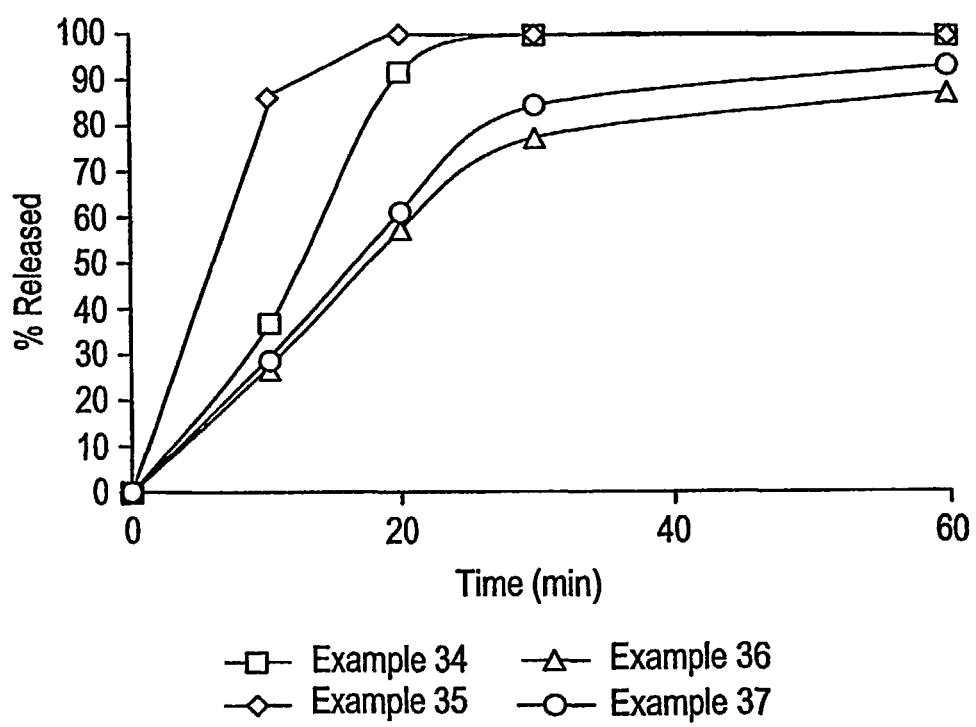
FIG. 6 is a graph showing improved dissolution rates for particles of the present invention.
Figure 7:
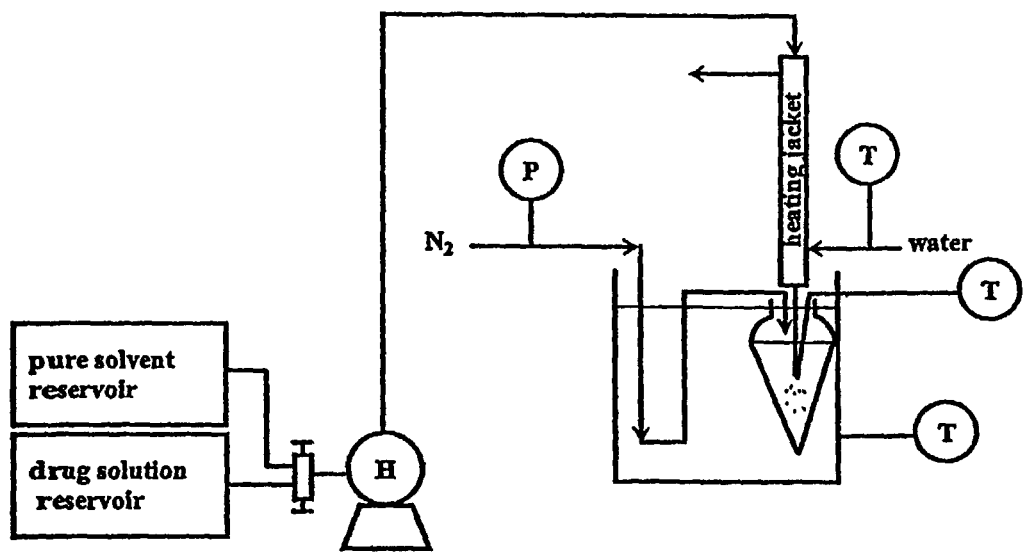
FIG. 7 is a depiction of an EPAS apparatus, where T-thermocouple, P=pressure regulator, and H=HPLC pump.
Figure 8:
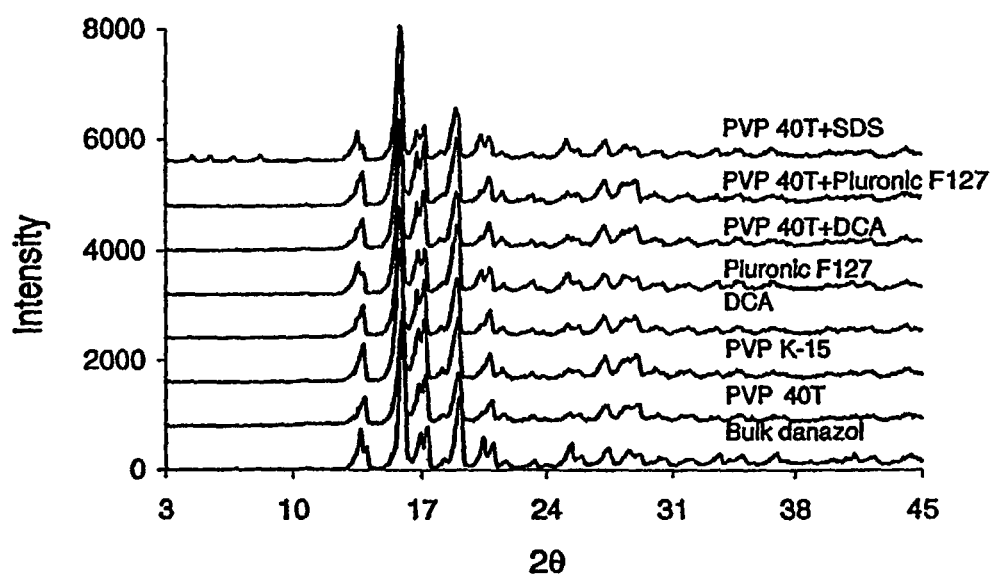
FIG. 8 is an x-ray profile of danazol systems.

The drug was nifedipine and the solvent was methylene chloride. The concentration of drug in the organic was 1.0 weight percent. In all cases the stabilizer in the aqueous solution was poly(vinyl alcohol) (PVA). The volume of the aqueous solution was 20 ml. Table H lists excipients added to the aqueous solution in addition to the PVA. In all cases the resulting aqueous drug suspension was rapidly frozen by dipping the sample container in liquid nitrogen and then lyophilized for 24 hours. The resulting powder was thoroughly mixed and dissolution studies were performed on these powders. The results of these dissolution tests were compared with that for bulk nifedipine. The results, shown in FIG. 6, clearly indicate the increased dissolution rates of EPAS processed nifedipine over the bulk unprocessed nifedipine. The crystallinity of these powders was also studied using X-ray diffraction patterns, with the Result being a reduction in crystallinity of the drug processed according to the present invention As compared to the bulk drug.

TABLE H

| Ex | Excipients in aqueous solution |
|----|-------------------------------|
| 34 | 1.5 wt percent PVP K40 |
| 35 | 1.5 wt percent SLS |
| 36 | 1 wt percent Poloxamer 407 |
| 37 | 1 wt percent PVP K15 |

Examples 38-39

The drug was ketoprofen and the solvent was methylene chloride. The temperature of the sprayed drug/organic mixture and the receiving aqueous solution was 87° C. The concentration of drug in the organic was 1.0 weight percent. The particle stabilizers in the aqueous solution are listed in Table 3. In all cases the concentration of the particle stabilizer in the aqueous solution was 2 weight percent and the organic solution contains, in addition to the drug, 0.5 weight percent Poloxamer 407. The volume of the aqueous solution was 20 ml. In all cases the resulting aqueous drug suspension was rapidly frozen by dipping the sample container in liquid nitrogen and then lyophilized for 24 hours. Crystallinity studies were performed on these powders using X-ray diffraction patterns, and were compared with that for bulk ketoprofen, which resulted in the processed powder exhibiting amorphous character as opposed to the bulk ketoprofen.

TABLE J

| Ex | Aqueous stabilizer |
|----|-------------------|
| 38 | Deoxycholic acid |
| 39 | SLS |

Examples 40-45

Danazol particles with high dissolution rates and extremely high drug:excipient ratios greater than about 5, corresponding to a potency (wt drug/wt drug+wt excipient) above 80% were produced by EPAS. An aqueous suspension was produced by EPAS to produce surfactant, or other excipient, coated particles with a low drug:excipient ratio ranging from 1:4 to 1:1. The suspension was then centrifuged and the supernatant was decanted to remove the free surfactant, or other excipient, in order to raise the potency in the precipitate. The adsorbed surfactant, or other excipient, was sufficient to prevent aggregation and enhance wetting to maintain a high surface area and likely a high local equilibrium concentration of API in the diffusion layer. The dissolution rate was analyzed as a function of the surfactant, or other excipient, adsorption, particle size, surface area, contact angle, particle morphology and crystallinity.

Materials

Danazol was purchased from Spectrum Chemicals & Laboratory Products Corporation (Cat# D1103). Pluronic F127 (BASF), Polyvinylpyrrolidone (PVP K-15, Mw=15,000 and PVP 40T, Mw=40,000) (Sigma, St. Louis, Mo.), Sodium dodecyl sulfate (Sigma) and Deoxycholic acid (Sigma) were used as received. HPLC grade acetonitrile was from Merck (Germany) and spectro grade dichloromethane was from Fisher Scientific Co. (NJ, USA)

Evaporative Precipitation into Aqueous Solution (EPAS)

The organic danazol solution was fed by an HPLC pump through a 3 m long 1/16 in. o.d.×0.030 in. i.d. stainless steel coiled tube contained within a 1½" OD×24" long plastic water jacket (Alltech). Water was circulated through the jacket with a JULABO MP temperature controller. The organic solution was atomized through an unheated insulated adjustable restrictor (5 mm dia.×136 mm long, ISCO, USA) into hot water. Atomization was achieved by adjusting the nozzle valve manually to maintain a pressure drop to about 3500 psi. The aqueous stabilizing solution was contained in a 250 ml plastic submerged in a temperature-controlled water bath. The nozzle was submerged approximately 10 cm under the surface of the aqueous solution. To suppress and drain the foam produced by the organic vapor, nitrogen was blown downwards on top of the foam at 20 psi into the cylinder through three 1/16 in. o.d.×0.030 in. i.d. stainless steel tubes. Unless indicated otherwise, the stabilizer was added in the aqueous phase and was not present in the organic feed solution. After spraying for a required time to produce the desired drug/excipient ratio, the suspension was recovered and analyzed within 30 mins to determine the particle size by light scattering with a Malvern Mastersizer-S (Malvern Instruments Ltd., U. K.).

Excipient Adsorption Measurement

To quantify excipient stabilization of the danazol particles in the EPAS suspension, excipient adsorption was measured based on a mass balance between the supernatant and precipitate. In these measurements, $W_{sw}$ was the weight of the supernatant before drying, which includes the weight of water, excipient and danazol, which may dissolve in micelles or excipient complexes if formed. $W_{sd}$ was the weight of the supernatant after drying, thus ($W_{sw}-W_{sd}$) was the amount of water in the supernatant. $W_{pw}$ was the weight of the precipitate before drying, which includes danazol, adsorbed excipient and a small amount of supernatant with the same composition as the bulk supernatant. $W_{pd}$ was the weight of the precipitate after drying. $W_{pdan}$ was the amount of danazol in the precipitate measured by HPLC. $W_{psurf}$ was the amount of adsorbed excipient on danazol. Since composition of the small amount of supernatant in the precipitate was assumed to be the same as that in the bulk supernatant $$\frac{W_{sd}}{W_{sw} - W_{sd}} = \frac{W_{pd} - W_{pdan} - W_{psurf}}{W_{pw} - W_{pd}} \quad (1)$$

From this equation, the amount of adsorbed excipient on danazol was given by $$W_{psurf} = W_{pd} - W_{pdan} - (W_{pw} - W_{pd}) \times \left(\frac{W_{sd}}{W_{sw} - W_{sd}}\right) \quad (2)$$

To measure the amount of excipient adsorbed on the particles, 1% w/v danazol solution in dichloromethane was sprayed into 15 ml aqueous solution containing 1% w/v excipient at a flow rate of 1 ml/min for 7.5 mins to produce a suspension with a drug to excipient ratio of 0.5:1. The pressure drop was 3000-4000 psi and the temperature was 75° C. After centrifugation, the supernatant and the precipitate were weighed before and after drying at 55° C. and −30 in. Hg.

High Potency Danazol Powder by Centrifugation

Two percent (2%) w/v danazol solution in dichloromethane was sprayed at a flow rate of 1 ml/min into 100 ml aqueous solution containing 1% w/v excipient or a excipient mixture at 1:1 w/w ratio, if two surfactants were used, to stabilize the drug particles. The temperatures of both heating jacket and water bath were 80° C. and the pressure drop was 3500-4000 psi. After 25 minutes spray, a suspension with drug to excipient ratio of 0.5 was recovered and the particle size of the danazol particles was measured with Malvern Mastersizer-S. The suspensions were centrifuged (BECKMAN, Model TJ-6, USA) at 3000 rpm for 30 mins. The supernatants were poured out and the precipitates were placed into a vacuum oven and dried at 40° C., and −30 in Hg for 3-4 hrs. The crystallinity of the dry powders was examined by x-ray diffraction (PW1720, PHILIPS). The surface area of the dry powders was measured with a high-speed surface area BET analyzer (NOVA 2000, Quantachrome Instruments, USA).

Dissolution Test

After centrifugation and vacuum drying, 20 mg dry powder was placed into a USP basket assembly and stirred at 50 rpm in pH 9.0 SDS/tris buffer, which contained 0.75 w/v % sodium dodecyl sulfate and 1.21 w/v % tris (hydroxymethyl) aminomethane PD 2960 in aqueous solution for 1 hour. The stirring rate was then increased to 200 rpm for 1 hour. Aliquots of the dissolution medium (5 ml) were sampled at 2, 5, 10, 20, 30, 60 and 120 mins. The aliquots were filtered through 0.45 μm syringe filters and 2 ml of each sample were diluted with 0.1 ml acetonitrile before analysis. Danazol concentrations were measured using HPLC (SHIMADZU, LC-600, Japan).

Particle Size

Particle size distributions, based on volume fraction, of the original EPAS suspension and redispersed dry powder were measured by static light scattering with a Malvern Mastersizer-S. To measure the particle size distribution, 5 ml suspension with 5 mg drug/ml water concentration, was diluted with 500 ml distilled water, to produce a light obscuration in the range of 10-30% for accurate measurement. To study the redispersibility of the dry powders after centrifugation and vacuum drying, about 50 mg dry powder were suspended into 500 ml distilled water to produce an obscuration in the range 10-30%. After 1 minute, the particle size distribution was measured. In a control experiment, bulk danazol was dispersed in 500 ml 0.02% non micelle-forming PVP 40T aqueous solution, since it was very hydrophobic and difficult to disperse in pure water. Ultrasound was used in the measurement to break up the agglomerated particles.

Contact Angle mg dry powder was filled into a 0.7 cm diameter flat faced die and compressed with a Carver Laboratory Press (Model M, Fred S. Carver Inc, WIS, USA) at 1500 kgf into a tablet. A drop of 51 μl distilled water was placed on the surface of the tablet and contact angle was measured from the tangential angle of the water drop with help of a camera (Panasonic WV-1410, Philippines).

Stressed Cycle Stability Study

Dry powders were placed in 60 ml Qorpak® glass bottles, sealed with sodium calcium aluminosilicate hydrate desiccant containing cobaltous chloride indicator (VWR International, West Chester, Pa.). The temperature cycle was: increase temperature from −5° C. to 40° C. over 30 mins, hold at 40° C. for 2.5 hours and then decrease temperature from 40° C. to −5° C. over 30 mins. The cycle was repeated 6 times per day. The humidity was dry and the duration of the stability study was 2 weeks. The characteristics of the dry powders were studied over two weeks.

Results and Discussion

Excipient Adsorption Study

The adsorption of various surfactants onto drug particle surfaces during EPAS are listed in Table K(1).

TABLE K(1)

Adsorption of excipient onto danazol in EPAS suspension

| Aqueous excipient | Properties | Chemical structure of excipients | $M_w$ of excipients | $W_s/W_d$ (m/m, %) |
|---|---|---|---|---|
| PVP K-15 | Homopolymer | [pyrrolidone repeat unit structure] | 15,000 | 13.0 ± 2.43 |
| PVP 40T | Homopolymer | | 40,000 | 10.0 ± 1.01 |
| Pluronic F127 | Copolymer | $HO(CH_2CH_2O)_{98}(CH_2CHO)_{67}(CH_2CH_2O)_{98}H$ <br> $\|$ <br> $CH_3$ | 12,528 | 3.87 ± 1.43 |
| Pluronic F127* | Copolymer | | 12,528 | 11.2 ± 0.72 |

TABLE K(1)-continued

Adsorption of excipient onto danazol in EPAS suspension

| Aqueous excipient | Properties | Chemical structure of excipients | $M_w$ of excipients | $W_{sf}/W_d$ (m/m, %) |
|---|---|---|---|---|
| DCA | Anionic surfactant | 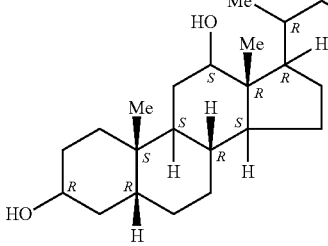 | 414 | 5.79 ± 1.61 |
| SLS | Anionic surfactant | $CH_3(CH_2)_{10}CH_2O{-}SO_2{-}ONa$ | 288 | 5.44 ± 0.46 |

*Adsorption measurement after 3 days storage at ambient conditions.

TABLE K(2)

Pluronic F127 adsorption on danazol particles after 3 days storage

| $W_{sw}$ (g) | $W_{sd}$ (g) | $W_{pw}$ (g) | $W_{pd}$ (g) | $W_{pdan}$ (mg) | $W_{psur}$ (mg) | $W_{psur}/W_{pdan}$ (%) |
|---|---|---|---|---|---|---|
| 1.8987 | 0.0414 | 0.1276 | 0.0200 | 15.820 | 1.888 | 11.9 |
| 1.5594 | 0.0373 | 0.0901 | 0.0213 | 17.753 | 1.862 | 10.5 |

Table M shows the concentration of danazol in the supernatant. For PVP 40T and PVP K-15, the concentration of danazol in the supernatant solution was on the order of the detection limit which was 0.02 μg/ml. The fraction of danazol in the aqueous suspension recovered in the precipitate after centrifugation was above 99%. For Pluronic F127, SDS and DCA, the recoveries decreased, but were still greater than 96.2% for each excipient except for SDS. After centrifugation and vacuum drying, the potency of danazol in the dry powders was higher than 83.2%, as shown in Table L. Drug:excipients ratios varied from 4:1 to 9:1.

TABLE L

Particle size of danazol in the suspension at excipient concentration was 1% w/v and its redispersibility after drying.

| Aqueous Excipients | D (v, 0.5) (μm) EPAS suspension | D (v, 0.5) (μm) suspension with ultrasonic | D (v, 0.5) (μm) redispersed dry powders w/o ultrasonic |
|---|---|---|---|
| Bulk Danazol | | | 29.63 21.07 (30s) |
| PVP K-15 | 29.47 | 15.27 (15s) 12.50 (30s) | 14.15 7.60 (30s) |
| PVP 40T | 49.28 | 13.82 (15s) 17.62 (30s) | 14.07 10.53 (30s) |
| PVP40T + SLS | 16.80 | 13.82 (30s) | 18.00 12.13 (30s) |
| Pluronic F127 | 80.35 | 32.29 (15s) 25.09 (30s) | 39.73 22.17 (30s) |
| DCA | 100.09 | 24.64 (30s) | 56.86 23.88 (30s) |
| SLS | 70.62 | 31.65 (15s) 27.50 (30s) | 61.14 29.32 (30s) |
| PVP 40T + Pluronic F127 | 125.92 | 28.75 (30s) | 71.73 26.16 (30s) |
| PVP40T + DCA | 121.77 | 28.02 (15s) 23.61 (30s) | 52.90 23.23 (30s) |

TABLE M

Concentration of danazol in the supernatant, recovery from the precipitate and its potency (g danazol/g powder) in the dry powders

| Aqueous excipient | $C_{ds}$ (mg/ml) | Danazol recovery (%) | Potency of danazol (%) |
|---|---|---|---|
| PVP K-15 | 0.0002 | 100 | 88.5 |
| PVP 40T | 0.0001 | 100 | 92.3 |
| Pluronic F127 | 0.035 | 99.3 | 89.3 |
| DCA | 0.084 | 98.3 | 85.1 |
| SLS | 0.804 | 82.1 | 83.2 |
| PVP 40T + Pluronic F127 | 0.009 | 99.8 | 91.5 |
| PVP 40T + DCA | 0.020 | 99.6 | 86.4 |
| PVP 40T + SLS | 0.191 | 96.2 | 92.9 |

Dissolution Rate

Figure 9:
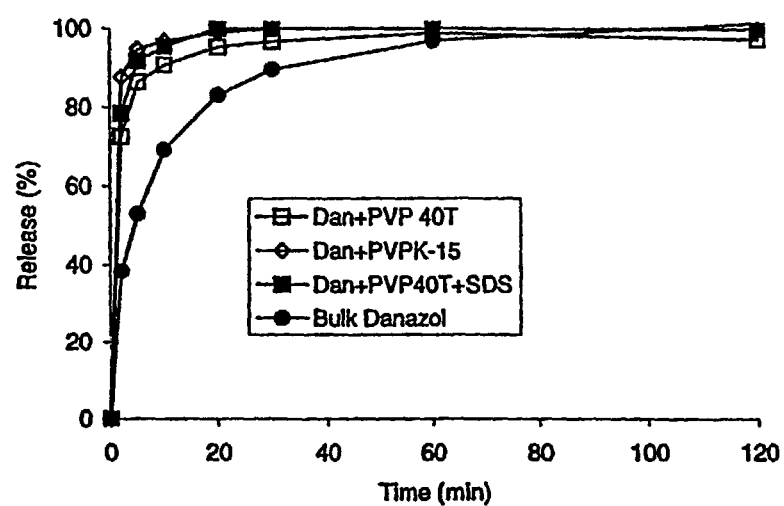
FIG. 9($b$) is a graph showing danazol systems with low dissolution rates.
Figure 9B:
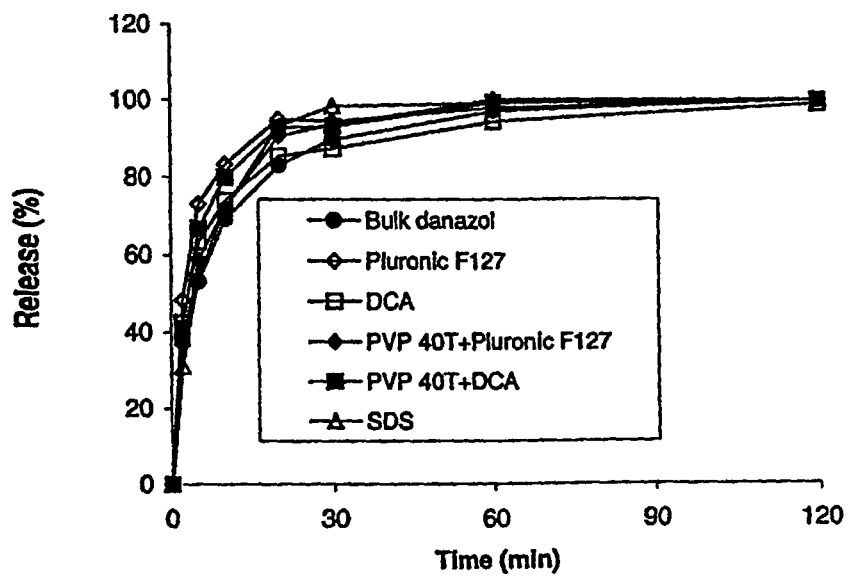

As shown in FIGS. 9(a) and 9(b), the dissolution rate was much higher for PVP K-15, PVP 40T or PVP 40T+SDS than the other stabilizers. In two mins, 70, 80 and 90% danazol was dissolved with PVP 40T, PVP K-15 or PVP 40T+SDS as the surfactants, respectively. For the other systems, the dissolution rates were much lower, closer to that of bulk danazol. We will show below that these systems had larger particle sizes and lower surface areas.

The effect of adsorbed excipient and free excipient on dissolution rate was studied by mixing PVP 40T precipitate from the centrifuged EPAS suspension with PVP 40T powder to form an overall drug to excipient ratio of 0.5. As shown in FIG. 9(a), the dissolution rate did not change. The changes in surface area, diffusion layer thickness and concentration of the API in bulk solution from the EPAS spray and adsorbed excipient were sufficient to produce high dissolution rates, without any need for mixing in additional stabilizer powder.

Particle Size Distribution and Redispersibility of the Dry Powders

The mean particle sizes of the EPAS suspensions, EPAS suspensions after sonication, and redispersed dry powders after centrifugation and vacuum drying are shown in Table L. The particle sizes, both with and without sonication, are correlated with the adsorption during the EPAS spray given in Table K.

X-Ray Diffraction

X-ray diffraction was used to analyze the crystallinity of the dry powders. As shown in FIG. 9, the crystallinity of danazol was lower for the vacuum dried precipitates from EPAS relatively to bulk danazol. The a-peak heights of danazol in different excipient systems at $2\theta=15°$ are listed in Table N. The reduction in crystallinity was less than 20% after correction for the presence of 10% w/w excipient. It was assumed that the danazol peak height was linear in concentration for a fixed weight. The degree of crystallinity for these samples did not appear to be correlated to the particle size or dissolution rates. Thus enhanced dissolution rates are possible even with only a modest reduction in crystallinity.

TABLE N

The peak height of danazol x-ray diffraction at $2\theta = 15°$

| Excipient | Peak height (counts) |
| --- | --- |
| Bulk danazol | 3182 |
| PVP K-15 | 2358 |
| PVP 40T | 1942 |
| Pluronic F127 | 2843 |
| DCA | 2413 |
| SLS | 2867 |
| PVP 40T + Pluronic F127 | 2546 |
| PVP 40T + DCA | 2371 |
| PVP 40T + SLS | 2465 |

Surface Area

The BET surface areas of the dry powders were analyzed. As shown in Table O, systems with small particle size and high dissolution rates, that is danazol with PVP K-15, PVP 40T or PVP 40T+SDS, had surface areas on the order of 5 $m^2/g$.

TABLE O

Surface area of the dry powder

| Excipient | Surface Area ($m^2/g$) |
| --- | --- |
| Bulk danazol | 0.52 |
| PVP K-15 | 5.55 |
| PVP 40T | 4.89 |
| PVP 40T + SLS | 4.98 |
| Pluronic F127 | 3.13 |
| DCA | 3.72 |
| SLS | 3.07 |
| PVP 40T + Pluronic F127 | 3.28 |
| PVP 40T + DCA | 3.22 |

Contact Angle

The contact angle results are shown in Table P. For systems with high dissolution rates, contact angles were close to the value of pure PVP, which was 43°, indicating high surface coverage by PVP. For the anionic excipient systems, the contact angles were very low. The overall contact angle may be written as $$\cos\theta = f_1 \cos\theta_1 + f_2 \cos\theta_2$$

where $f_1$ and $f_2$ are the fractions of the surface occupied by surface types having contact angles $\theta_1$ and $\theta_2$. The contact angles in Table P are below the values expected from this equation, based on the pure component values $\theta_1$ and $\theta_2$, indicating that the surface was enriched by the hydrophilic excipient.

TABLE P

Contact angle of dry powder after centrifugation and drying

| Excipient | Contact angle (°) | |
| --- | --- | --- |
| Bulk danazol | 61.5 | 61.0 |
| PVP K-15 | 41.8 | 40.4 |
| PVP 40T | 48.8 | 47.0 |
| Pluronic F127 | 34.0 | 34.0 |
| DCA | 19.9 | 17.8 |
| SLS | 7.0 | |
| PVP 40T + Pluronic F127 | 42.0 | 37.5 |
| PVP 40T + DCA | 34.0 | 36.2 |
| PVP 40T + SLS | 14.6 | 13.2 |

Cyclic Stability Study

Two week cyclic stability tests were undertaken under harsh storage conditions for the three systems with the highest dissolution rates. Samples were analyzed each week to determine if the potency, particle size, crystallinity, dissolution rate and morphology had changed with time. The concentrations of danazol in the three systems were: 88.9% with SD (standard deviation) of 2.9% in PVP K-15+Danazol, 93.6% with SD of 1.4% in PVP 40T+Danazol and 89.6% with SD of 5.0% in PVP 40T+SDS+Danazol.

Redispersibility of the Dry Powder

Figure 10:
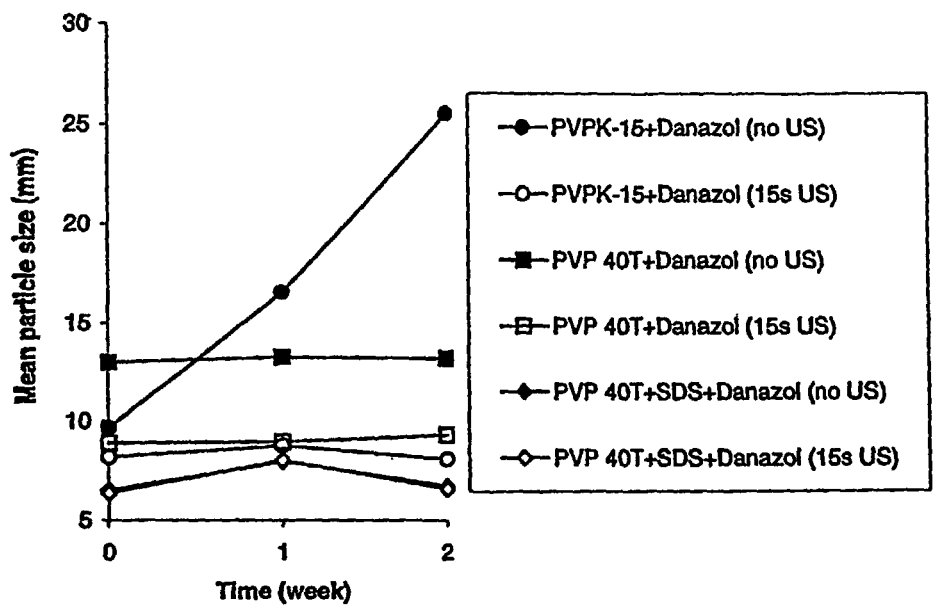
FIG. 10 is a graph reflecting the particle redispersibility in the stability study period.

The dry powders were redispersed into 500 ml pure water. Changes over two weeks are shown in FIG. 10. Without ultrasound, the size of particles stabilized with PVP K-15 increased from 9.7 μm to 25.5 μm after two weeks. However, after 15 seconds sonication, the primary particle size decreased to 8 μm for both samples. For the PVP K-15 system, agglomeration of the dry particles increased with time. These agglomerates were broken into primary particles with ultrasound. The moisture in the container was minimal due to desiccant.

X-Ray Diffraction

Figure 11:
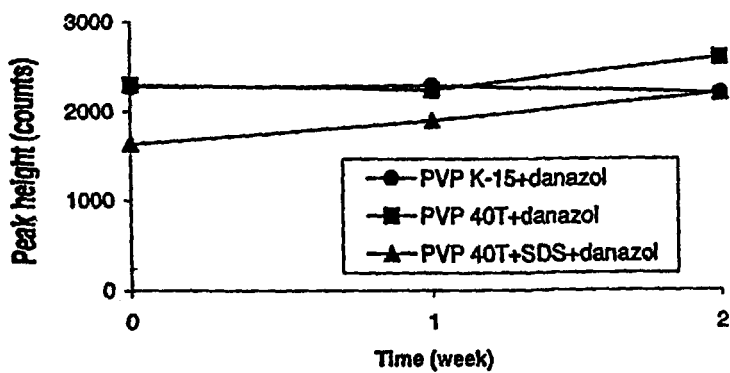
FIG. 11 is a graph showing the x-ray peak height of danazol samples during the stability study.

X-ray diffraction was used to study the crystallinity of the dry powders. As shown in FIG. 11 shows the diffraction profiles of danazol over 2 weeks.

Surface Area

Figure 12:
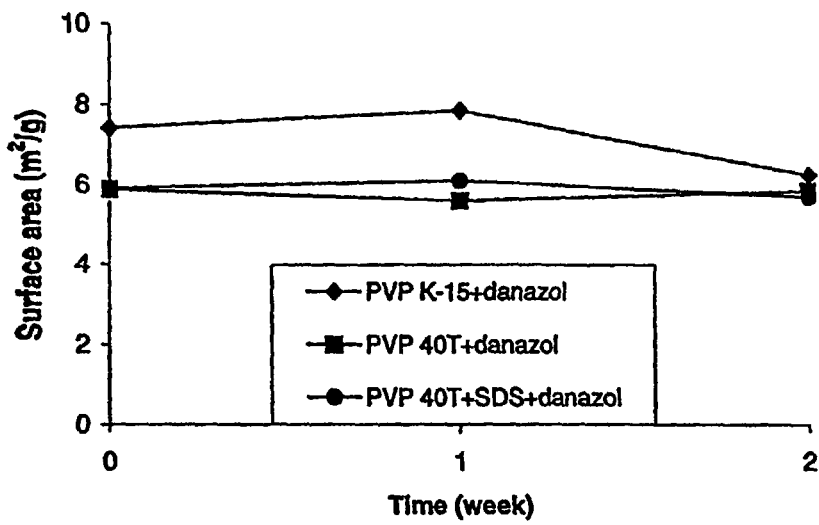
FIG. 12 is a graph depicting the surface area of danazol systems during the stability study.
Figure 14:
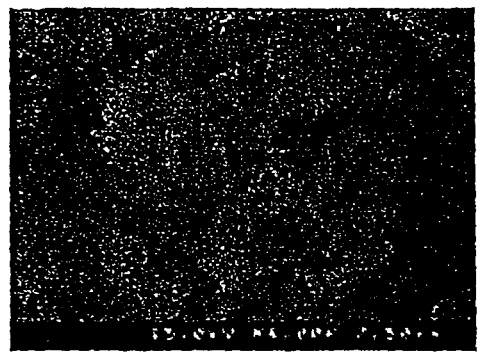
FIG. 14 are SEMs showing danazol samples.
Figure 14:
Figure 14:

FIG. 12 shows the surface area of danazol systems over time. This result was in accord with the stability of the drug particle size over time. FIG. 14 shows that danazol with PVP 40T+SLS has a smooth crystal surface, but with PVP K-15 or PVP 40T it has a fluffy Surface, despite the similar crystallinities.

Dissolution Rates

The dissolution results are shown in FIG. 13. The dissolution rate did not change over time, nor did other certain properties of these drug powders, including the particle size and surface area. For the two week cyclic stability study, high potency danazol dry powders with PVP K-15, PVP 40T or PVP 40T and SDS as stabilizing excipients were very stable when desiccant was used to prevent to the particles from the moisture.

What is claimed is:

1. A method of producing poorly water soluble drug particles for release comprising the steps of:
providing a drug;
providing a container comprising aqueous solution;
spraying the drug and one or more excipients below the surface level of the aqueous solution wherein the one or more excipients selected from polyoxyethylene sorbitan monolaurate, phosphatidyl choline, a poly(ethylene)-poly(propylene) copolymer, sodium lauryl sulfate (SLS), Poly(vinyl pyrrolidone) (PVP), Poloxamer, polyoxyethylene monostearate, gelation agent, deoxycholic acid, poly(vinyl alcohol) (PVA), cetostearyl alcohol, methylcellulose, hydroxyethylcellulose, hydroxypropylcellulose, hydroxypropylmethylcellulose phthalate, noncrystalline cellulose, magnesium aluminum silicate, and triethanolamine;

forming one or more stabilized drug particles by solution precipitation, anti-solvent precipitation, spray freezing, evaporative precipitation or lyophilization;

separating said one or more stabilized drug particles from a suspension solution;

removing said solution from the one or more stabilized drug particles; and producing one or more stabilized drug particles having a drug-to-excipient ratio of greater than about 4:1 and an average particle diameter from 50 nanometers to about 20 microns; and a dissolution rate greater than about 65% drug in about 60 minutes;

wherein the drug-to-excipient ratio is about 2:1, 3:1, 4:1, 5:1, 6:1, 7:1, 8:1, 9:1, 10:1 or greater;

wherein the drug particles have a surface area greater than about 2.5 $m^2/g$, 5 $m^2/g$, 10 $m^2/g$, 20 $m^2/g$ or 30 $m^2/g$; and wherein the drug potency is about 80% or 100%.

2. The method of claim 1, wherein the drug particles are separated by centrifugation, settling, or filtering.

3. The method of claim 1, wherein the step of removing the solution from the resulting drug particles comprises lyophilization, vacuum dried, or spray drying, or spray drying.

4. The method of claim 1, wherein the amount of drug dissolved is about 80%, 85%, 90%, 95% or 100%.

5. The method of claim 4, wherein the dissolution occurs about 5, 7, 10, 15, 20, 25 or 30 times faster than the bulk drug.

\* \* \* \* \*